United States Patent [19]
Vladimirsky

[11] Patent Number: 5,389,075
[45] Date of Patent: Feb. 14, 1995

[54] SINGLE-USE HYPODERMIC SYRINGE

[76] Inventor: Roman Vladimirsky, 2700 N. Cahuenga Blvd., #3109, Los Angeles, Calif. 90068

[21] Appl. No.: 76,469

[22] Filed: Jun. 14, 1993

[51] Int. Cl.$^6$ ............................................. A61M 5/00
[52] U.S. Cl. ................................................. 604/110
[58] Field of Search ............... 604/110, 218, 187, 228, 604/221

[56] References Cited
U.S. PATENT DOCUMENTS 4,973,308  11/1990  Borras et al. ................... 604/228 X
5,149,323   9/1992  Colonna ......................... 604/218 X
5,201,709   4/1993  Capra et al. ........................ 604/110

Primary Examiner—John D. Yasko
Attorney, Agent, or Firm—Allan M. Shapiro

[57] ABSTRACT

The single-use hypodermic syringe has a body in the form of a hypodermic syringe cylinder with a needle connection on the front. A piston in the cylinder draws in and discharges liquid. The plunger is connected to the piston by means of a collar which permits withdrawal of the piston. When the plunger returns the piston, a spring deflects to release the collar so that a second withdrawal stroke is prevented.

11 Claims, 3 Drawing Sheets

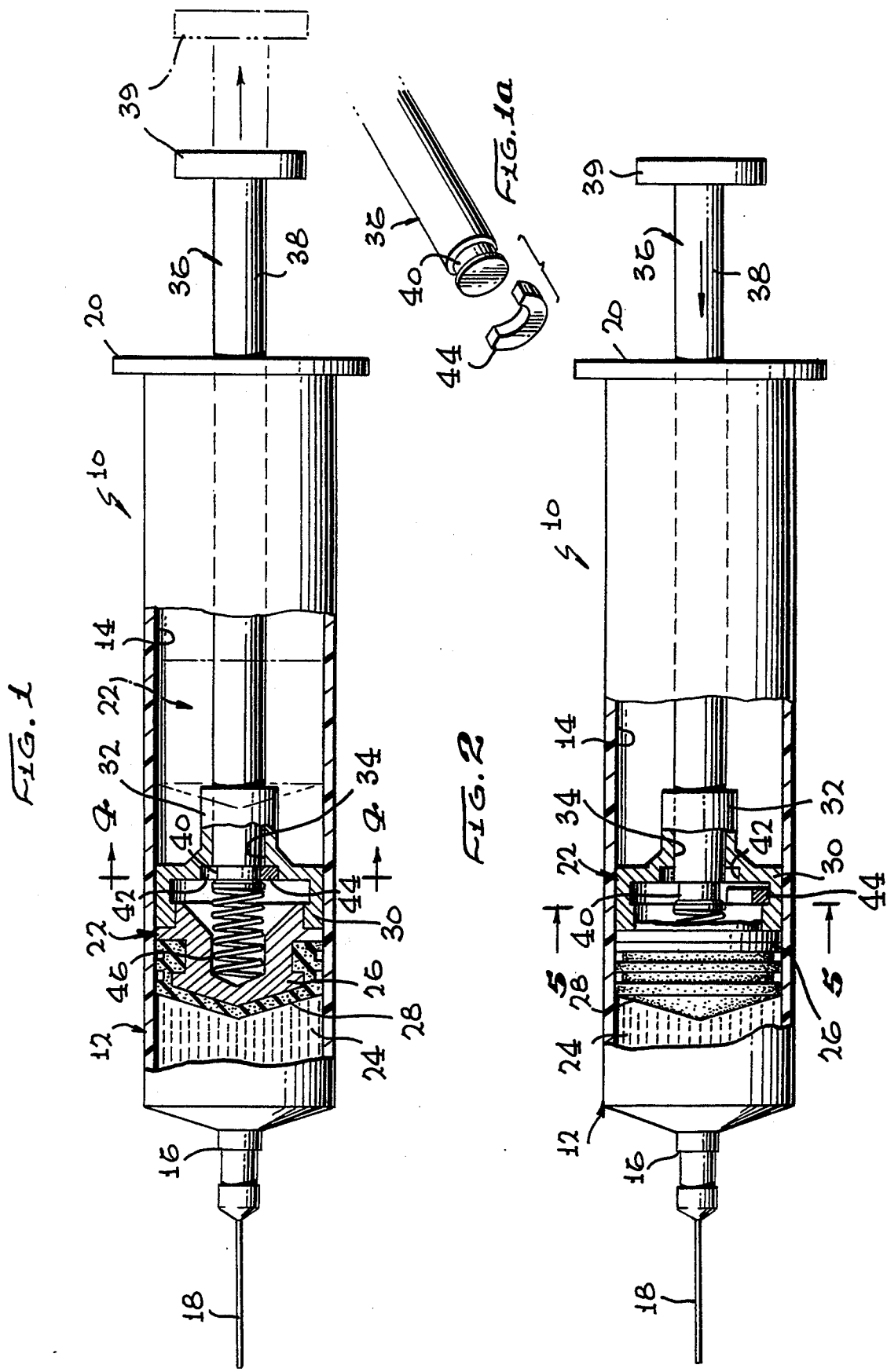

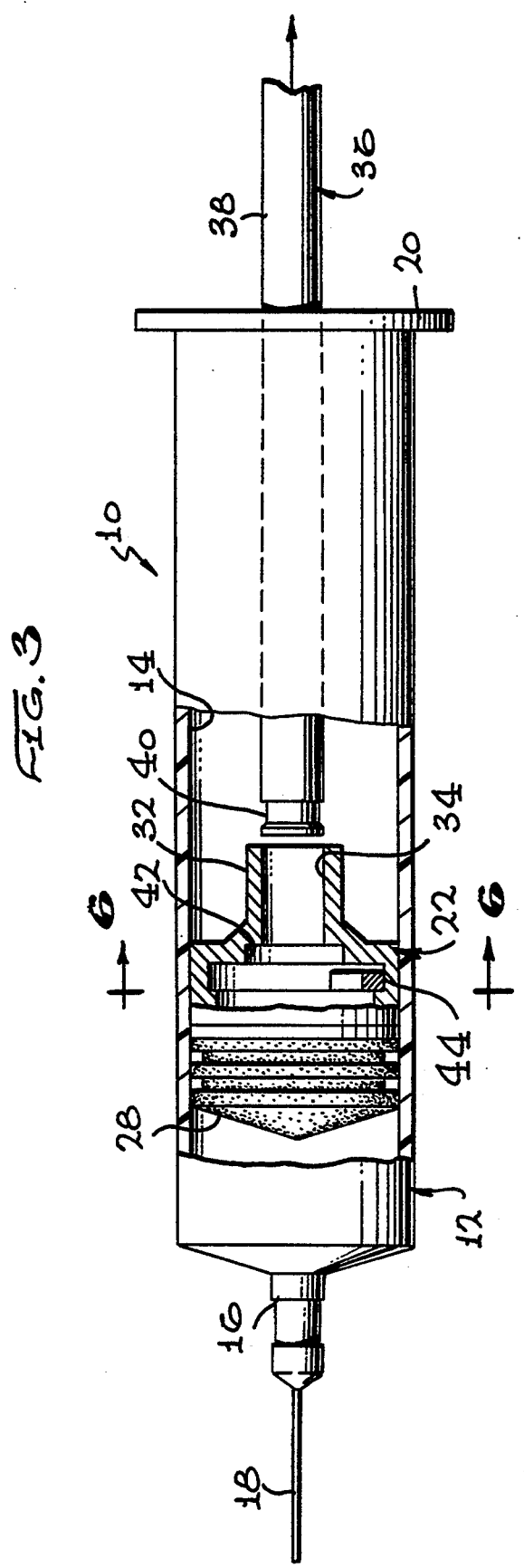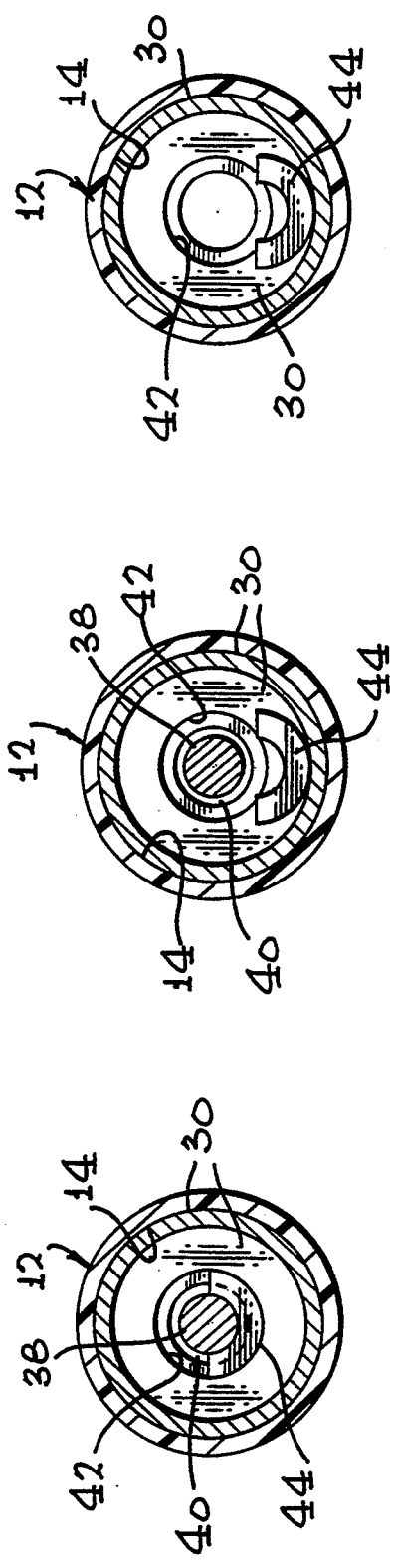

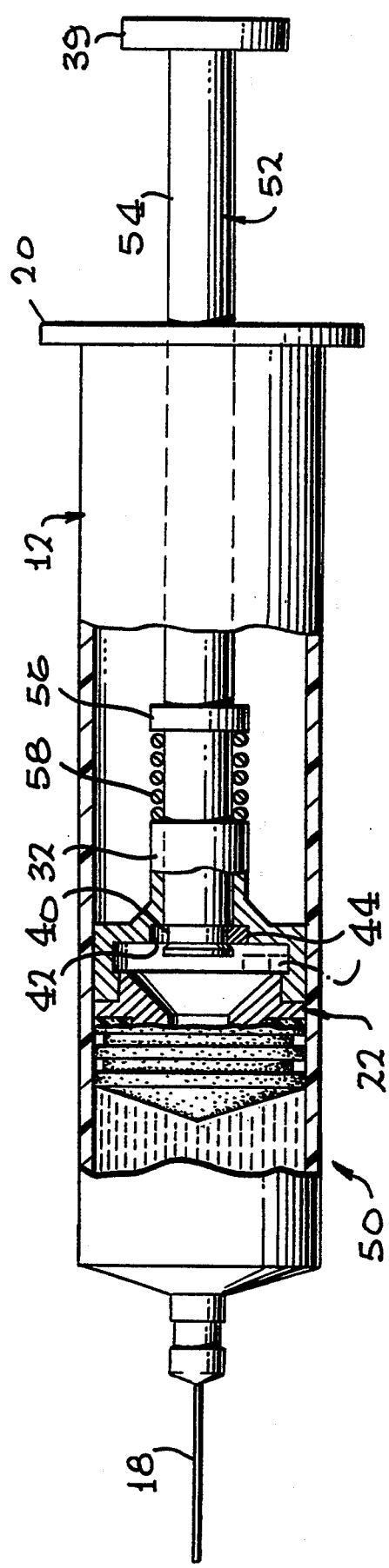
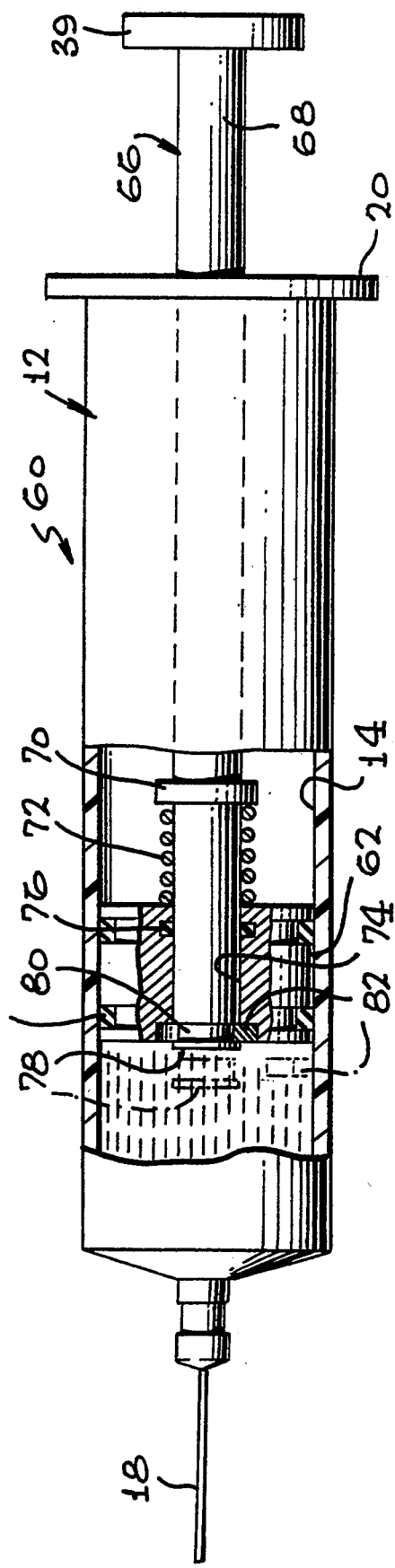

SINGLE-USE HYPODERMIC SYRINGE

FIELD OF THE INVENTION

This invention is directed to a single-use hypodermic syringe wherein the plunger is connected to the piston by means of a collar which falls free when the plunger moves the piston on the forward stroke.

BACKGROUND OF THE INVENTION

Hypodermic syringes are widely used in the field of medicine for withdrawing body fluids for tests or for delivering medicine to the body. Syringes are supplied in sterile condition and are normally intended for only a single use, in order to avoid any risk of contamination. The reuse of syringes, even those expected to go through a sterilization protocol, was favorable for the spreading of very serious infectious diseases such as AIDS or Hepatitis-B. The use of single-use sterilized hypodermic syringes overcame most of these risks because hospital personnel reliably disposed of the syringes after use.

A more dangerous situation occurs in the multiple use of syringes outside of the hospital where illegal drugs are injected in non-sanitary conditions. Under these circumstances, hypodermic syringes may be used on multiple occasions among several persons. This improper usage led to the spread of infectious diseases among the illegal drug-utilizing population. In order to reduce these risks, it is desirable to provide a syringe which disconnects the piston from the plunger after a single-use cycle.

SUMMARY OF THE INVENTION

In order to aid in the understanding of this invention, it can be stated in essentially summary form that it is directed to a single-use hypodermic syringe wherein the syringe barrel contains a piston. The plunger is connected to the piston by means of a collar which is held in place by a spring. When the plunger is pressed in to move the piston forward in the barrel and express liquid from the barrel, the plunger force overcomes the spring force to allow the collar to fall free and disconnect the piston from the plunger. Subsequent plunger withdrawal movement does not move the piston.

It is, thus, an object of this invention to provide a single-use hypodermic syringe which properly operates while drawing liquid into the hypodermic syringe barrel and discharges the liquid therefrom, but which prevents further stroking of the piston by the plunger.

It is another object and advantage of this invention to provide a single-use hypodermic syringe which is of economic construction so that it can be widely used as a single-use device.

It is a further object and advantage of this invention to provide a single-use hypodermic syringe wherein the plunger is reliably disconnected from the piston after a single cycle of use.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is a side-elevational view of the first preferred embodiment of the single-use hypodermic syringe of this invention, with parts broken away and parts taken in section during the withdrawal stroke of the plunger and piston.

FIG. 1A is an isometric view of the forward end of the plunger and its collar.

FIG. 2 is similar to FIG. 1, but showing the piston and plunger on the return stroke where fluid is discharged from the syringe barrel.

FIG. 3 is a view similar to FIG. 2 showing the disconnection which occurs when the plunger is subsequently withdraw.

FIG. 4 is a section taken generally along line 4—4 of FIG. 1.

FIG. 5 is a section taken generally along line 5—5 of FIG. 2.

FIG. 6 is a section taken generally along line 6—6 of FIG. 3.

FIG. 7 is a side-elevational view, with parts broken away and parts taken in section, of a second preferred embodiment of the single-use hypodermic syringe of this invention.

FIG. 8 is a side-elevational view, with parts broken away and parts taken in section, of a third preferred embodiment of the single-use hypodermic syringe of this invention.

DESCRIPTION OF THE PREFERRED EMBODIMENTS

The first preferred embodiment of the single-use hypodermic syringe of this invention is generally indicated at 10 in FIGS. 1, 2 and 3. The syringe 10 has a barrel 12 and has an interior cylindrical bore 14. The forward end of the syringe barrel is closed except for needle fitting 16. The needle fitting is configured to receive the base of hypodermic needle 18. The rear end of the barrel carries finger flange 20 to aid in the manipulation of the syringe 10.

Piston 22 is slidably mounted within the bore 14 and closes the rearward end of the bore to define fluid space 24. The fluid space 24 is only open out through the needle 18. Piston 22 is made up of piston body 26, which carries piston cover 28 thereon. The piston cover 28 is of resilient material so that it seals with respect to bore 14, but permits sliding motion of the piston. The resilient piston cover engages in a groove in the piston body to be retained thereon. Piston flange 30 is a flange which slidably fits within bore 14. The flange 30 has a forward circular member which is permanently attached to the piston body 26. Boss 32 is formed on the flange 30 and extends rearwardly in the syringe barrel. Plunger opening 34 extends through the boss.

Plunger 36 has a piston rod 38 which extends from rear thumb pad 39 forward through the plunger opening 34 to a position within piston flange 30. The piston rod has a groove 40 adjacent the forward thereof, see FIGS. 2 and 3. Piston flange 30 has a circular recess 42 therein. Half-annular collar 44 normally lies both within the groove 40 and the recess 42, as seen in FIGS. 1 and 4. This locks the piston rod into the piston flange 30. Thus, the plunger controls the piston in the barrel. Compression spring 46, which is engaged within piston body 26 and acts against the forward end of piston rod 38, retains the parts in place in which the collar 44 is constrained within its groove 40 and recess 42.

The single-use hypodermic syringe 10 is supplied with its piston 22 in the forward position with the fluid space 24 at a minimal volume. The user thrusts the needle 18 into the fluid to be taken into the needle, and then the plunger is withdrawn. Withdrawal forces move the plunger in the direction of the arrow in FIG. 1, and fluid is drawn into the space 24. In the usual case, the now-filled hypodermic syringe 10 is taken to a different location and its contents are expelled.

Pressing down on the plunger in the direction of the arrow in FIG. 2 causes leftward force on piston rod 38, which slightly compresses the spring 46. This moves the piston rod to the left with respect to the piston so that the collar 44 is moved out of its recess 42 and thence falls out of its groove 40 into the space therearound, as seen in FIG. 2. Even though the collar 44 is out of its groove, expulsion of the fluid contents from the syringe fluid contents from the syringe fluid space can continue because the piston rod moves the piston the left, as seen in FIG. 2. If there was an attempt to draw fluid into the syringe again, the piston rod 38 would pull out of the bore 34 in boss 32, as seen in FIG. 3. The collar being out of its groove 40 permits this freedom. As seen in FIG. 3, the groove 40 can be chamfered on the left to aid in release of the collar 44. In this way, the syringe 10 can be used only once.

A second preferred embodiment of the single-use hypodermic syringe of this invention is generally indicated at 50 in FIG. 7. Syringe 50 has the same barrel 12, needle 18 and piston 22. In this case, the plunger 52 has a piston rod 54 which carries thereon a flange 56. The flange is spaced from boss 32, and a compression spring 58 is positioned therebetween. The compression spring 58 urges the plunger to the right with respect to the piston to retain half-annular collar 44 in the groove 40 in the forward end of the piston rod 54 and in the recess 42 in the piston 22.

The syringe 50 is supplied with the piston and plunger in the forward position. When fluid is drawn into the barrel by withdrawal of the piston by pulling on the plunger, the collar 44 locks the piston rod to the plunger. When the fluid is expressed by pushing in on the plunger, spring 58 is compressed and the groove 40 moves forward out of recess 42. At that point, the collar 44 drops out of groove 40. The plunger can continue to move the piston forward until the expressing of fluid is complete. If, at any time, the plunger is not thrust forward, the expressing of fluid stops. However, more fluid can be expressed simply by thrust on the plunger. The collar 44 need not be positioned in its groove 40 in this direction of stroke. When the expressing stroke is completed, withdrawal of the plunger will not withdraw the piston, but the piston rod 54 will simply pull out of the piston. In this way, the syringe 50 is a single-use hypodermic syringe.

The third preferred embodiment of the single-use hypodermic syringe of this invention is generally indicated at 60 in FIG. 8. The syringe 60 has the same barrel 12 and needle 18, but has a different piston and plunger than the syringe 10 or the syringe 50. Piston 62 slides in the bore 14 and is sealed with respect thereto by means of O-ring 64 or other suitable sliding seal devices. Plunger 66 has a piston rod 68 which is generally straight and cylindrical of uniform thickness. Along the length of the piston rod, it carries flange 70. Beyond flange 70 is compression spring 72 which engages against the piston and the flange to urge the plunger to the right with respect to the piston. The piston rod continues through bore 74 in the piston to be slidable therein. O-ring 76 provides a fluid seal in the sliding joint. The piston 62 has a recess 78 in its forward end. Aligned with the recess is groove 80 in the forward end of the piston rod. Half-annular collar 82, the same as collar 44, occupies the recess 78 and groove 80. As long as the force of the plunger 66 is to the right, in the direction to draw fluid into the fluid space in the barrel, the groove 80 stays in recess 78 to retain collar 82. This force is maintained by spring 72.

When fluid is drawn into the fluid space in the barrel by drawing the plunger to the right, collar 82 remains in place and couples the plunger to the piston. This coupling continues while the plunger is drawn to the right, pulling the piston with it. When the fluid in the syringe barrel is to be expelled, the plunger is thrust to the left. The force to push the piston to the left is greater than the compression force of spring 72. This causes the piston rod to move to the left with respect to the piston, freeing the collar 82. The collar falls out to the dashed-line position shown in FIG. 8. Pressing the plunger to the left continues to move the piston to the left expelling the fluid in the space. When this step is complete, the plunger cannot be used to withdraw the piston because the piston rod is no longer coupled to the piston by means of collar 82. The piston rod and plunger are free so that the syringe cannot be reused. In this way, a single-use hypodermic syringe is provided.

This invention has been described in its presently contemplated best modes, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A single-use hypodermic syringe comprising:
   a barrel, attachment means on said barrel for connecting to said barrel a fluid-handling structure for permitting fluid to be drawn into and discharged from said syringe barrel;
   a piston in said syringe barrel to draw fluid into and discharge fluid from said syringe barrel by motion of said piston in said syringe barrel, a piston rod opening in said piston and a recess in said piston adjacent said piston rod opening;
   a plunger for controlling said piston in said barrel, said plunger including a piston rod engaged in said piston rod opening in said piston, a groove in said piston rod adjacent said recess; and
   a half annular collar engaged in said recess and in said groove, said collar being sized to be retained in said groove when said collar is in said recess and to be free of said groove when said collar is out of said recess so that after one stroke of said piston by said plunger away from said fluid connection means and toward said fluid connection means, said collar comes out of said recess and said groove so that said piston is free of said piston rod to prevent further actuation of said piston by said piston rod.

2. The single-use hypodermic syringe of claim 1 wherein a spring is engaged between said piston and said piston rod to urge said piston rod with respect to said piston in a direction to retain said collar in said recess.

3. The single-use hypodermic syringe of claim 2 wherein there is a flange on said piston rod and there is a compression spring engaged between said flange and said piston to urge said piston rod in a direction to retain said collar in said recess.

4. The single-use hypodermic syringe of claim 2 wherein said spring is a compression spring engaged between said piston and said piston rod to urge said piston rod in a direction to retain said collar in said recess.

5. The single-use hypodermic syringe of claim 4 wherein said compression spring is positioned within said piston.

6. A single-use hypodermic syringe comprising:
   a barrel, said barrel having an interior bore therein, means on said barrel for the connection of a fluid device thereon for permitting fluid to be drawn into and discharged from fluid space in said bore;
   a piston in said bore, said piston being slidable within said bore and sealed with respect to said bore to define fluid space in said bore;
   a plunger connected to said piston for drawing said piston through said bore to enlarge said fluid space in said bore and for moving said piston to reduce fluid space in said bore to cause fluid flow into and out of said fluid space, said piston having a plunger opening therein, said plunger having a piston rod therein sized to slide in said plunger opening, said piston having a recess therein adjacent said plunger opening, said recess facing toward said fluid space, a groove in said piston rod, said groove lying in said recess when said piston is connected to said plunger; and
   a half annular collar of substantially rectangular cross section engaged in both said groove and said recess to lock said piston to said plunger during the withdrawal stroke of said plunger wherein said piston moves to enlarge said fluid space, said piston rod being movable with respect to said piston so that upon motion of said piston rod to move said collar out of said recess, said collar becomes free of engagement with said groove so that said piston rod and said plunger are free of said piston.

7. A single-use hypodermic syringe comprising:.
   a barrel, said barrel having an interior bore therein, means on said barrel for the connection of a fluid device thereon for permitting fluid to be drawn into and discharged from fluid space in said bore;
   a piston in said bore, said piston being slidable within said bore and sealed with respect to said bore to define fluid space in said bore;
   a plunger connected to said piston for drawing said piston through said bore to enlarge said fluid space in said bore and for moving said piston to reduce fluid space in said bore to cause fluid flow into and out of said fluid space, said piston having a plunger opening therein, said plunger having a piston rod therein sized to slide in said plunger Opening, said piston having a recess therein adjacent said plunger opening, said recess facing toward said fluid space, a groove in said piston rod, said groove lying in said recess when said piston is connected to said plunger; and
   a collar engaged in both said groove and said recess to lock said piston to said plunger during the withdrawal stroke of said plunger wherein said piston moves to enlarge said fluid space, a spring engaged between said piston rod and said plunger to urge said piston rod in a direction to retain said collar in said recess, said piston rod being movable with respect to said piston so that, upon motion of said piston rod to move said collar out of said recess, said collar becomes free of engagement with said groove so that said piston rod and said plunger are free of said piston.

8. A single-use hypodermic syringe comprising:
   a barrel, said barrel having an interior bore therein, means on said barrel for the connection of a fluid device thereon for permitting fluid to be drawn into and discharged from fluid space in said bore;
   a piston in said bore, said piston being slidable within said bore and sealed with respect to said bore to define fluid space in said bore;
   a plunger connected to said piston for drawing said piston through said bore to enlarge said fluid space in said bore and for moving said piston to reduce fluid space in said bore to cause fluid flow into and out of said fluid space, said piston having a plunger opening therein, said plunger having a piston rod therein sized to slide in said plunger opening, said piston having a recess therein adjacent said plunger opening, said recess facing toward said fluid space, a groove in said piston rod, said groove lying in said recess when said piston is connected to said plunger; and
   a collar engaged in both said groove and said recess to lock said piston to said plunger during the withdrawal stroke of said plunger wherein said piston moves to enlarge said fluid space, said piston rod being movable with respect to said piston so that, upon motion of said piston rod to move said collar out Of said recess, said collar becomes free of engagement with said groove so that said piston rod and said plunger are free of said piston, said groove being chamfered on its wall away from said recess to aid in departure of said collar from said groove.

9. The single-use hypodermic syringe claim 8 wherein a spring is engaged between said piston rod and said plunger to urge said piston rod in a direction to retain said collar in said recess.

10. The single-use hypodermic syringe claim 6 wherein a spring is engaged between said piston rod and said plunger to urge said piston rod in a direction to retain said collar in said recess.

11. The single-use hypodermic syringe of claim 6 wherein said groove is chamfered on its wall away from said recess to aid in departure of said collar from said groove.

* * * * *